(12) United States Patent
Wu

(10) Patent No.: US 9,370,202 B2
(45) Date of Patent: Jun. 21, 2016

(54) ENCAPSULATED METAL ION NANOCLUSTERS

(71) Applicant: LG Bionano, LLC, Wilmington (DE)

(72) Inventor: Chien-Chin Wu, Wilmington (DE)

(73) Assignee: LG Bionano, LLC, Wilmington, DE (US)

( * ) Notice: Subject to any disclaimer, the term of this patent is extended or adjusted under 35 U.S.C. 154(b) by 348 days.

(21) Appl. No.: 13/833,279

(22) Filed: Mar. 15, 2013

(65) Prior Publication Data

US 2014/0271473 A1    Sep. 18, 2014

(51) Int. Cl.
| | | |
|---|---|---|
| *A61K 49/00* | (2006.01) | |
| *A23L 1/304* | (2006.01) | |
| *A61K 9/51* | (2006.01) | |
| *A61K 9/00* | (2006.01) | |
| *A61K 47/48* | (2006.01) | |
| *A61K 33/26* | (2006.01) | |
| *B82Y 5/00* | (2011.01) | |

(52) U.S. Cl.
CPC ............... *A23L 1/3045* (2013.01); *A23L 1/304* (2013.01); *A61K 9/0087* (2013.01); *A61K 9/5123* (2013.01); *A61K 33/26* (2013.01); *A61K 47/48015* (2013.01); *B82Y 5/00* (2013.01)

(58) Field of Classification Search
CPC ...................................................... A23L 1/304
See application file for complete search history.

(56) References Cited

U.S. PATENT DOCUMENTS

| | | | |
|---|---|---|---|
| 5,624,668 A | 4/1997 | Helenek et al. | |
| 6,342,257 B1 | 1/2002 | Jacobson et al. | |
| 6,599,498 B1 | 7/2003 | Groman et al. | |
| 7,005,531 B2 | 2/2006 | Justus et al. | |
| 7,179,939 B2 | 2/2007 | Rangisetty et al. | |
| 7,612,109 B2 | 11/2009 | Geisser et al. | |
| 7,674,780 B2 | 3/2010 | Newton et al. | |
| 7,871,597 B2 | 1/2011 | Groman et al. | |
| 7,943,664 B2 | 5/2011 | Powell et al. | |
| 7,964,568 B2 | 6/2011 | Beck et al. | |
| 8,030,480 B2 | 10/2011 | Gharpure et al. | |
| 8,053,470 B2 | 11/2011 | Xiao et al. | |
| 8,263,577 B2 | 9/2012 | Reim et al. | |
| 2003/0232084 A1 | 12/2003 | Groman et al. | |
| 2005/0037996 A1* | 2/2005 | Beck ............... A61K 31/191 514/59 |
| 2006/0199972 A1 | 9/2006 | Johnson et al. | |
| 2006/0293220 A1 | 12/2006 | Holt | |
| 2007/0161600 A1 | 7/2007 | Helenek et al. | |
| 2008/0176941 A1 | 7/2008 | Xiao et al. | |
| 2010/0009901 A1 | 1/2010 | Rabovsky et al. | |

FOREIGN PATENT DOCUMENTS

| | | |
|---|---|---|
| CN | 1798754 | 5/2004 |
| WO | WO-96/06101 | 2/1996 |
| WO | WO-2010/007441 | 1/2010 |
| WO | WO-2012/054376 | 4/2012 |

OTHER PUBLICATIONS

Holt, et al., "Ability of a beta casein phosphopeptide to modulate the precipitation of calcium phosphate by forming amorphous dicalcium phosphate nanoclusters", Biochemical Journal, 314:1035-1039 (1996).
Chertow, et al., "Update on adverse drug events associated with parenteral iron", Nephrol. Dial. Transplant., 21 (2): 378-382 (2006).
Rodgers, et al., "High-Molecular Weight Iron Dextran: A Wolf in Sheep's Clothing?", J. Am Soc. Nephrol, 19: 833-834, 2008.
Wyck, "Labile Iron: Manifestations and Clinical Implications", J. Am Soc. Nephrol, 15: S107-S111, 2004.

\* cited by examiner

*Primary Examiner* — Paul Dickinson
(74) *Attorney, Agent, or Firm* — Cesari and McKenna LLP

(57) ABSTRACT

A metal ion nanocluster having a formula of $X(OH)_a Y_b Z_c M_d (H_2O)_e$. X, Y, Z, M, a, b, c, d, and e are defined herein. The nanocluster has a particle size of 2 to 500 nm and a molecular weight of 3500 to 1000000 Dalton. Also disclosed are a composition containing the nanocluster and a method of preparing the nanocluster.

25 Claims, No Drawings

ENCAPSULATED METAL ION NANOCLUSTERS

BACKGROUND

Many minerals useful for treating mineral deficiency are only soluble as metal ions, which in general are irritating to tissues and have an unpleasant taste. Metal complexes have been used instead to address this problem.

Metal complexes, usually having a high turbidity point and a low acid dissociation rate, are unstable in neutral or acidic conditions desired for oral and intramuscular applications. As such, they are typically formulated in a basic solution. For example, Venofer, an iron sucrose commercial product that must only be administered via the intravenous route, has a pH value as high as 11, making it unsuitable for beverages and pharmaceutical formulations other than intravenous injections.

There is a need to develop metal complexes that are stable in neutral or acidic conditions.

SUMMARY

This invention is based on the discovery of stable metal ion nanoclusters that have a low turbidity point and a high acid dissociation rate.

In one aspect, this invention features a metal ion nanocluster having a particle size of 2 to 500 nm (e.g., 2 to 150 nm and 2 to 80 nm), a molecular weight of 3500 to 1000000 Dalton (e.g., 5000 to 300000 Dalton and 10000 to 180000 Dalton), a turbidity point of 8 or lower (e.g., 7 or lower and 4.5 or lower), and a dissociation rate of 1 to 180 minutes (e.g., 1 to 60 minutes). A turbidity point refers to a pH point at which precipitation occurs during a pH titration. A dissociation rate refers to the time required to dissociate greater than 75% of nanoclusters into free metal ions in a 0.75 M HCl aqueous solution at 37° C. with stirring.

The metal ion nanocluster of this invention has a formula of $X(OH)_a Y_b Z_c M_d (H_2 O)_e$.

X is a metal cation. Examples include, but are not limited to, cations of Cr, Al, Bi, Zn, Ba, Cu, Ti, Mg, Mn, Pt, Ca, Se, In, Fe, Co, Ni, V, La, Mo, Sr, Zr, and a combination thereof. Preferably, the metal cation is Mg(II), Al(III), Ca(II), Cr(III), Cu(II), Zn(II), Mn(II), Ti(IV), Fe(II/III), Co(II), Ni(II), Bi(III), V(V), La(III), Mo(VI), Sr(II), Zr(IV) or a combination thereof. Y is a water-soluble salt-forming anion, which can be an inorganic anion or an organic anion. Examples include, but are not limited to, fluoride, chloride, bromide, iodide, nitrate, sulfate, acetate, and a combination thereof. Preferably, it is chloride, nitrate, sulfate, acetate, or a combination thereof. Z is a water-soluble ligand. Examples include, but are not limited to, a carbohydrate, a hydrogenated carbohydrate, a hydrolyzed carbohydrate, a polyol, a polyether, and a combination thereof. Preferably, it is xylitol, mannitol, ribose, mannose, xylose, galactose, fructose, lactose, glucose, isomaltose, isomalt, sucrose, maltitol, trehalose, arabinose, sorbitol, polyisomaltose, isomalto-oligosaccharide, dextrin, dextran, fructooligosaccharide, or a combination thereof. M is a turbidity point modifier. Examples include, but are not limited to, a complex-forming polyvalence anion, an oxidized carbohydrate (e.g., gluconic acid, sodium gluconate, and gluconate ester), a carboxylated polyol, a carboxylated polyether, a sulfonated carbohydrate, a sulfonated polyol, a sulfonated polyether, a phospholated carbohydrate, a phospholated polyol, a phospholated polyether, an amino acid, a water-soluble polypeptide, a water-soluble protein, and a combination thereof. Examples of the complex-forming polyvalence anion include, but are not limited to, citrate, malate, fumarate, tartrate, lactate, oxalate, succinate, ascorbate, phosphate, pyrophosphate, glycerophosphate, or a combination thereof.

The term "carbohydrate" refers to a monosaccharide (e.g., xylose, arabinose, glucose, mannose, fructose, galactose, and ribose), a disaccharide (e.g., sucrose, lactose, maltose, and isomaltose), an oligosaccharide (i.e., carbohydrates that are composed of 3-9 monosaccharide residues joined through glycosidic linkage, such as raffinose, melezitose, maltotriose, acarbose, stachyose, fructooligosaccharide, and galactooligosaccharides), or a polysaccharide (e.g., dextrin, dextran, poltisomaltose, and maltodextrin).

Referring back to formula $X(OH)_a Y_b Z_c M_d (H_2 O)_e$, a is 0.1 to 20 (e.g., 1 to 10), b is 0 to 9 (e.g., 0.1 to 9, 0 to 3, and 0.1 to 3), c is 0.1 to 10 (e.g., 1 to 6), d is 0.1 to 9 (e.g., 0.1 to 6), and e is 0 to 25 (e.g., 0 to 10).

Another aspect of this invention relates to a composition containing the nanocluster described above. This composition, a transparent aqueous solution or a water-soluble solid for reconstitution into a transparent aqueous solution, is free of unchelated ions, unreactive water-soluble ligands, and labile low-molecular-weight ion complexes (i.e., below 3500 Dalton). The pH value of the transparent aqueous solution can be 3 to 11.5, e.g., 3.5 to 9. A transparent aqueous solution refers to a clear or translucent aqueous solution, i.e., a colloidal solution or a colloidal suspension.

Also within the scope of this invention is a method for treating a disorder or for detecting a tissue image by administering to a subject in need thereof an effective amount of the nanocluster described above. Examples of the disorder include a mineral deficiency disorder, a gastric reflux disorder, and a chronic renal failure. The tissue image is for use in differentiating an abnormal tissue from a normal tissue.

The term "treating" or "treatment" refers to administering a nanocluster to a subject, who has an above-described disorder, a symptom of such a disorder, or a predisposition toward such a disorder, with the purpose to confer a therapeutic effect, e.g., to cure, relieve, alter, affect, or ameliorate the above-described disorder, any symptom of it, or the predisposition toward it.

Still within the scope of this invention is a method of preparing the nanocluster described above. The method includes the steps of (1) providing an aqueous dispersion containing X, Y, Z, and OH; (2) adjusting the pH of the aqueous dispersion to a predetermined value to obtain a pH-adjusted aqueous dispersion; (3) heating the pH-adjusted aqueous dispersion to 50-180° C. so that a nanocluster is formed; and (4) adding M after any of the above steps. Note that M becomes an integral part of the nanocluster thus formed. The ratio of X:Y:Z:M, all of which are defined above, is 1:0-9:0.1-10:0.1-9. The nanocluster thus formed in an aqueous solution can be collected by nanofiltration and then dried (e.g., in an oven, by vacuum, by spray, and by freeze) to yield a solid nanocluster.

The details of one or more embodiments of the invention are set forth in the description below. Other features, objects, and advantages of the invention will be apparent from the description and from the claims.

DETAILED DESCRIPTION

Described herein are metal ion nanoclusters each containing one or more metal cations, one or more water-soluble salt-forming anions, one or more water-soluble ligands, and one or more turbidity point modifiers.

Any metal cation having a dietary or health benefit can be used in a nanocluster of this invention. Examples include Mg(II), Al(III), Ca(II), Cr(III), Cu(II), Zn(II), Mn(II), Ti(IV), Fe(II/III), Co(II), Ni(II), Bi(III), V(V), La(III), Mo(VI), Sr(II), and Zr(IV). More than one cations, e.g., Fe(III) and Mg(II), can be included in the nanocluster.

A suitable water-soluble salt-forming anion can be either organic or inorganic, e.g., fluoride, chloride, bromide, iodide, nitrate, sulfate, and acetate.

A suitable ligand is soluble in water and binds to a metal cation to form a nanocluster of this invention. Examples include xylitol, mannitol, ribose, mannose, xylose, galactose, fructose, lactose, glucose, isomaltose, isomalt, sucrose, maltitol, trehalose, arabinose, sorbitol, polyisomaltose, isomalto-oligosaccharide, dextrin, dextran, and fructooligosaccharide. More examples are described in U.S. Patent Application Publication 2012/0093898.

A turbidity point modifier is used to adjust the turbidity point of a nanocluster to a predetermined range, e.g., 7 or lower, and thereby making the nanocluster stable in a neutral or acidic solution, an important feature of intramuscular injections or oral formulations. Further, a turbidity point modifier shortens the time for preparing a nanocluster. It can also lower the temperature required in the preparation process. turbidity point modifier, which interacts with a metal cation(s), an anion(s), or a ligand(s), is an integrated part of a nanocluster. A turbidity point modifier in a nanocluster can be a complex-forming polyvalent anion that is different from the water-soluble salt-forming anion therein. Examples of a polyvalent anion include citrate, malate, fumarate, tartrate, lactate, oxalate, succinate, ascorbate, phosphate, pyrophosphate, and glycerophosphate. Among them, citrate, oxalate, succinate, and tartrate are preferred.

A nanocluster of this invention can be prepared using various methods. In one embodiment, it is obtained by mixing a water soluble metal salt (e.g., ferric chloride), a ligand (e.g., xylitol), an alkaline agent (e.g., sodium hydroxide), and a turbidity point modifier (e.g., sodium citrate) in water at a suitable temperature (e.g., 50-180° C. or preferably 65-105° C.) for a predetermined process time (e.g., 30 minutes to 10 hours). Alternatively, the metal salt, the ligand, and the alkaline agent are mixed and heated to form a nanocluster precursor. A turbidity point modifier is then introduced to the precursor with or without heating (e.g., 50-180° C. and 65-105° C.). The type and amount of the turbidity point can be adjusted to obtain the nanocluster having a predetermined turbidity point.

The nanocluster thus formed is in an aqueous solution, which can be isolated using nanofiltration to obtain a concentrated nanocluster-containing solution, free of unchelated metal cations, unreactive ligands, and labile low-molecule-weight ion complexes. Note that unchelated metal cations are irritating to tissues and have an unpleasant metallic taste. They can also cause protein precipitation and interfere with physiological functions. Unreactive ligands increase microbial contamination and osmolarity of the solution. Labile low-molecular-weight ion complexes, which dissociate and diffuse into tissues fast, cause oxidative damage. See Wyck, Journal of American Society of Nephrology, 15, S107-11 (2004).

The concentrated nanocluster-containing solution is optionally dried to yield a nanocluster solid using a suitable drying method, e.g., oven drying, vacuum drying, spray drying, and freeze drying. The nanocluster solid can be reconstituted to a nanocluster solution without changing the turbidity point and other properties.

Below is an exemplary procedure for preparing a nanocluster of this invention. A metal cation and an anion, as a salt or a salt mixture, are mixed with a water-soluble ligand in an aqueous solution to give a solution or dispersion. The pH is adjusted using an alkaline salt or a base. The pH-adjusted solution or dispersion is heated until a nanocluster precursor is formed or until the solution or dispersion turns clear. A turbidity point modifier is then added to the precursor and heated to 50-105° C. to yield the nanocluster, which is isolated through nanofiltration and then dried in an oven to obtain a nanocluster solid. Other separation techniques such as solvent-induced precipitation (e.g., using a water-soluble organic solvent such as ethanol) can also be applied. The resulting solid product can be reconstituted into nanocluster colloidal solutions or formulated into other dosage forms.

The nanocluster thus formed typically has a turbidity point of 8 or lower (e.g., 4.5 or lower), which can be determined by the procedure described in Example 1 below or by analogous procedures, and a particle size of 2 nm to 500 nm (e.g., 2-80 nm), which can be determined by dynamic laser light scattering technique as described in B. J. Berne et al., "Dynamic Light Scattering," J. Wiley and Sons, Inc., New York, 1976; P. J. Freud et al., "A New Approach to particle Sizing by Dynamic Light Scattering," Microtrac, Inc.; and M. N. Trainer et al., "High-concentration submicron particle size distribution by dynamic light scattering," American Laboratory, July 1992.

Having a low turbidity point, a nanocluster of this invention is compatible with many physiological and excipient components. It can be formulated with these components in solid or liquid form. A solid composition containing a nanocluster can be conveniently used to prepare beverage, paste, jelly, capsules, or tablets. On the other hand, a liquid composition containing a nanocluster, which can be a transparent or translucent solution, can be used to prepare injectable or oral formulations.

A composition containing a nanocluster of this invention can be a dietary supplement, a cosmetic product, a contrast imaging product, or a pharmaceutical formulation. As a dietary supplement, additional nutrients, such as minerals, amino acids, or herb extracts, may be included. As a cosmetic product, additional ingredients, such as humectants, whitening agents, anti-oxidants, or herb extracts, may be included. As a contrast imaging product (e.g., for detecting a tissue image), it can be formulated into oral or injection dosage form with suitable pharmaceutically acceptable carrier. Heavy metal compositions and magnetic metal compositions are widely used for imaging purpose (e.g., an iron-containing composition as an MRI contrast agent and a barium-containing composition as an X-ray radio-contrast agent). As a pharmaceutical formulation (in forms including but not limited to powder, capsule, tablet, emulsion, aqueous suspension, dispersion, and solution), a nanocluster composition can be used alone or in combination with a pharmaceutically acceptable carrier. The carrier in a contrast imaging product or a pharmaceutical composition must be "acceptable" in the sense of being compatible with the active ingredient of the formulation (and, preferably, capable of stabilizing it) and not deleterious to the subject to be treated. Examples include lactose, colloidal silicon dioxide, magnesium stearate, sodium lauryl sulfate, and D&C Yellow #10. A lubricating agent, such as magnesium stearate, is typically added. For oral administration in a capsule form, useful diluents include lactose and dried corn starch. When an aqueous suspension or an emulsion is administered orally, a nanocluster composition can be suspended or dissolved in an aqueous phase combined with an emulsifying or suspending agent. If desired, a sweetening, flavoring, or coloring agent can be added.

A nanocluster composition can also be a food product, i.e., a liquid, solid, or semi-solid material that is used for nourishing humans or animals, for sustaining normal or accelerated growth, or for maintaining stamina or alertness. Examples include tea-based beverages, juice, coffee, milk, jelly, cookies, cereals, bread, donut, bagel, chocolates, snack bars, herbal extracts, dairy products (e.g., ice cream, and yogurt), soy bean product (e.g., tofu), and rice products.

Nanocluster compositions that contain iron can be used to treat iron deficiency disorders such as iron deficiency anemia. Compositions that contain chromium can be used to treat diabetes (such as type II diabetes), lower cholesterol level, and treat obesity. Those containing magnesium and aluminum/iron can be used as antacids, and those containing Mg, Mn, Cr, Zn, and Cu ions, can be used as total parenteral nutrition injections.

Further, this invention covers a method of administering an effective amount of a nanocluster composition to a patient having a disease described in the summary section above. The nanocluster composition can also be used for diagnosis (e.g., imaging), as a phosphate binder, or as an antacid for gastric reflux disorder.

"An effective amount" refers to the amount of a nanocluster composition that is required to confer a therapeutic effect on the treated subject. Effective doses will vary, as recognized by those skilled in the art, depending on the types of diseases treated, route of administration, excipient usage, and the possibility of co-usage with other therapeutic treatment.

The term "administering" covers oral, topical, or parenteral delivery to a subject a composition of the invention in any suitable form, e.g., food product, beverage, tablet, capsule, suspension, lotion, cream, gel, and solution. The term "parenteral" refers to subcutaneous, intracutaneous, intravenous, intramuscular, intraarticular, intraarterial, intrasynovial, intrasternal, intrathecal, intralesional, and intracranial injection, as well as various infusion techniques. A sterile injectable composition, e.g., a sterile injectable aqueous or oleaginous suspension, can be formulated according to techniques known in the art using suitable dispersing or wetting agents (such as Tween 80) and suspending agents, if necessary. The sterile injectable preparation can also be a sterile injectable solution or suspension in a non-toxic parenterally acceptable diluent or solvent, for example, as a solution in 1,3-butanediol, propylene glycol, or glycerine. Among the acceptable vehicles and solvents that can be employed are xylitol, mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

The nanocluster described above can be preliminarily screened for their efficacy in treating above-described diseases by an in vitro assay and then confirmed by animal experiments and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Composition 1, an exemplary composition of this invention, was prepared following the procedure described below. In a vessel equipped with a stirring and heating device, an aqueous solution was obtained by dissolving in 87 grams of water the following agents: (1) 13.68 grams of xylitol as a water-soluble ligand, (2) 2.18 grams of sodium gluconate as a turbidity point modifier, and (3) 27 grams of ferric chloride hexahydrate both as a metal cation and a water-soluble salt-forming anion. After the aqueous solution was heated to between 75 and 80° C., NaOH (12 grams in 54 grams of water) was added followed by heating at 90° C. for 30 minute to yield composition 1 containing ferric hydroxide xylitol gluconate nanoclusters.

Comparative composition 1' was prepared following exactly the same procedure described above except that no sodium gluconate was added.

Turbidity Point Assay

The turbidity points of composition 1 and 1' were measured by the method described in the USP monograph of Iron Sucrose Injection, USP28-NF23, page 1064. The pH value of composition 1 was adjusted to about 6.0 using 0.1 M hydrochloric acid solution. A light source was applied to the solution such that the light beam shone through the solution. More hydrochloric acid solution was added dropwise until a slight but lasting turbidity had developed. The pH value at this point was the turbidity point.

The results are shown in the table below. As demonstrated in the table, composition 1, which contained gluconate, a turbidity point modifier, had a turbidity point unexpectedly much lower than that of comparative composition 1', which did not contain any turbidity point modifier.

Note that the table below also shows turbidity points of compositions 2-6, each of which contains a turbidity point modifier, and comparative compositions 2', 3', 5', and 6', each of which does not contain any turbidity point modifier. Unexpectedly, each of compositions 2-6 had a turbidity point much lower than that of its corresponding comparative composition, i.e., one of comparative compositions 2', 3', 5', and 6'. Note that composition 3' is the corresponding comparative composition for composition 4.

Turbidity points of nanocluster compositions

| Composition | Turbidity point |
|---|---|
| 1 | Below 1 |
| 1A | Below 1 |
| Comparative 1' | 7.1 |
| 2 | 4.7 |
| 2' | 7.3 |
| 3 | 1.9 |
| 3' | 6.1 |
| 4 | 3.1 |
| 5 | 3 |
| 5' | 7.2 |
| 6 | 5 |
| 6' | 4 |

Example 1A

Composition 1A was prepared by separating the nanoclusters contained in composition 1 from the aqueous solution via nanofiltration with a molecular weight cut-off at 5000 Dalton. The separated nanoclusters were dried at 90° C. for 16 hours to yield composition 1A as a solid.

To demonstrate that solid composition 1A could be reconstituted into a nanocluster solution, composition 1A was dissolved in water to form a transparent nanocluster solution, which had the same turbidity point as that of composition 1. See the table above. Like composition 1, composition 1A unexpectedly has a turbidity point much lower than that of comparative composition 1'.

Example 2

Composition 2 was prepared following the procedure described below. In a vessel equipped with a stirring and heating device, an aqueous solution was obtained by dissolving in 87 grams of water the following agents: (1) 18.2 grams of mannitol as a water-soluble ligand, (2) 2.94 grams of sodium citrate dihydrate as a turbidity point modifier, and (3) 27 grams of ferric chloride hexahydrate both as a metal cation and a water-soluble salt-forming anion. After the aqueous solution was heated to between 75 and 80° C., NaOH (12 grams in 54 grams of water) was added followed by heating at 90° C. for 30 minute to yield composition 2 containing ferric hydroxide mannitol gluconate nanoclusters.

Comparative composition 2' was prepared following exactly the same procedure as composition 2 except that no sodium citrate dihydrate was added.

The turbidity points of both compositions 2 and 2' were measured following the procedure described in Example 1. The results, shown in the table above, unexpectedly demonstrate that composition 2 had a turbidity point much lower than that of comparative composition 2'.

Examples 3 and 4

To obtain compositions 3 and 4, comparative composition 3' was prepared following the procedure described below. In a vessel equipped with a stirring and heating device, a ferric hydroxide carbonate suspension was prepared by mixing a ferric nitrate nonahydrate solution (102 grams in 250 grams of water) and a sodium carbonate solution (55 grams in 350 grams of water). Solid sucrose (230 grams) and a NaOH solution (5 grams in 13 gram of water) were added. The resulting mixture was heated at 92° C. for 3 hours to obtain comparative composition 3' containing ferric hydroxide sucrose nanoclusters.

Composition 3 was prepared by mixing 0.5 grams of comparative composition 3' with 0.0683 grams of sodium oxalate.

On the other hand, composition 4 was prepared by mixing 0.5 grams of comparative composition 3' with 0.117 grams of sodium succinate.

The turbidity points of compositions 3, 3', and 4 were measured following the procedure described in Example 1. The results, shown in the table above, unexpectedly demonstrate that compositions 3 and 4 each had a turbidity point much lower than that of their comparative composition, i.e., composition 3'.

Example 5

Composition 5 was prepared following the procedure described below. In a vessel equipped with a stirring and heating device, a ferric hydroxide carbonate precipitate was obtained by mixing a ferric nitrate nonahydrate solution (25.6 grams in 62 grams of water) and a sodium carbonate solution (13 grams in 75 grams of water). Solid sucrose (60.8 grams) and solid sodium tartrate (4.6 grams) were added. The resulting mixture was heated at 92° C. for 1 hour to yield composition 5 containing ferric hydroxide sucrose tartrate nanoclusters.

Comparative composition 5' was prepared following exactly the same procedure as composition 5 except that a NaOH solution (5.05 grams in 13 grams of water) was used instead of solid sodium tartrate.

The turbidity points of both compositions 5 and 5' were measured following the procedure described in Example 1. The results, shown in the table above, unexpectedly demonstrate that composition 5 had a turbidity point much lower than that of comparative composition 5'.

Example 6

To obtain composition 6, comparative composition 6' was prepared following the procedure described below. In a vessel equipped with a stirring and heating device, a ferric chloride solution (150 grams in 1000 grams of water) and a sodium carbonate solution (96 grams in 544 grams of water) were mixed to yield a ferric hydroxide carbonate precipitate, which was isolated and washed by centrifugation to obtain 328 grams of a concentrated precipitate. Solid sucrose (545 grams) and a NaOH solution (12 grams in 108 grams of water) were added. The resulting mixture was heated at 105° C. for 10 hours to obtain comparative composition 6' containing ferric hydroxide sucrose nanoclusters.

Composition 6 was prepared by mixing 10 grams of comparative composition 6' with a sodium citrate dihydrate solution (0.5 grams in 1.5 grams of water) and heating at 80° C. for 30 minutes.

The turbidity points of both compositions 6 and 6' were measured following the procedure described in Example 1. The results, shown in the table above, unexpectedly demonstrate that composition 6 had a turbidity point much lower than that of comparative composition 6'.

Dissociation Assay

In addition, the dissociation rates of both compositions 6 and 6' were measured following the procedure described below.

The acid dissociation rate of composition 6 was determined according to the method described in U.S. Pat. No. 8,058,076. First, a solution of composition 6 was added into a volumetric flask, followed by the addition of 0.75 M hydrochloric acid solution at 37° C. After mixing, the solution was measured using a UV/VIS spectrophotometer at 450 nm every 5 minutes, starting at time 0 until a constant absorbance was observed by the spectrophotometer. The percentage concentration was calculated using the equation described at column 4 of U.S. Pat. No. 8,058,076. The acid dissociation rate (T75) was the time in minutes required to release 75% of the ferric ion from the composition. Composition 6 had an acid dissociation rate of 32 minutes.

Following the same procedure described above, comparative composition 6' had an acid dissociation rate of 27.6 minutes.

Unexpectedly, composition 6 had a lower acid dissociation rate than that of comparative composition 6'.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A metal ion nanocluster having a particle size of 2 to 500 nm, a molecular weight of 3500 to 1000000 Dalton, and a formula of $X(OH)aY_bZ_cM_d(H_2O)_e$, in which X is a metal cation, Y is a water-soluble salt-forming anion, Z is a water-soluble ligand, M is a turbidity point modifier, a is 0.1 to 20, b is 0 to 9, c is 0.1 to 10, d is 0.1 to 9, and e is 0 to 25, wherein the metal cation is Mg(II), Al(III), Ca(II), Cr(III), Cu(II), Zn(II), Mn (II), Ti(IV), Fe(II/III), Co(II), Ni(II), Bi(III), V(V), La(III), Mo(VI), Sr(II), Zr(IV), or a combination thereof; the turbidity point modifier is a complex-forming polyvalence anion, a carboxylated polyol, a carboxylated polyether, a sulfonated carbohydrate, a sulfonated polyol, a sulfonated polyether, a phospholated carbohydrate, a phospholated polyol, a phospholated polyether, an amino acid, a water-soluble polypeptide, a water-soluble protein, or a combination thereof; and the nanocluster has a turbidity point of 8 or lower.

2. The nanocluster of claim 1, wherein the particle size is 2 to 150 nm.

3. The nanocluster of claim 2, wherein the particle size is 2 to 80 nm.

4. The nanocluster of claim 1, wherein the water-soluble salt-forming anion is fluoride, chloride, bromide, iodide, nitrate, sulfate, acetate, or a combination thereof; the water-soluble ligand is a carbohydrate, a hydrogenated carbohydrate, a hydrolyzed carbohydrate, a polyol, a polyether, or a combination thereof; and the turbidity point modifier is a complex-forming polyvalence anion.

5. The nanocluster of claim 4, wherein the water-soluble salt-forming anion is chloride, nitrate, sulfate, acetate, or a combination thereof; the water-soluble ligand is xylitol, mannitol, ribose, mannose, xylose, galactose, fructose, lactose, glucose, isomaltose, isomalt, sucrose, maltitol, trehalose, arabinose, sorbitol, polyisomaltose, isomalto-oligosaccharide, dextrin, dextran, fructooligosaccharide, or a combination thereof; and the complex-forming polyvalence anion is citrate, malate, fumarate, tartrate, lactate, oxalate, succinate, ascorbate, phosphate, pyrophosphate, glycerophosphate, or a combination thereof.

6. The nanocluster of claim 1, wherein the nanocluster has a turbidity point of 4.5 or lower.

7. The nanocluster of claim 1, wherein a is 1 to 10, b is 0 to 3, c is 1 to 6, d is 0.1 to 6, and e is 0 to 10.

8. The nanocluster of claim 1, wherein the nanocluster has a molecular weight of 5000 to 300000 Dalton.

9. The nanocluster of claim 8, wherein the nanocluster has a molecular weight of 10000 to 180000 Dalton.

10. The nanocluster of claim 1, wherein the nanocluster has a dissociation rate of 1 to 180 minutes.

11. The nanocluster of claim 10, wherein the nanocluster has a dissociation rate of 1 to 60 minutes.

12. The nanocluster of claim 1, wherein the nanocluster has a particle size of 2 to 150 nm, a turbidity point of 7 or lower, and a dissociation rate of 1 to 180 minutes; the water-soluble salt-forming anion is fluoride, chloride, bromide, iodide, nitrate, sulfate, acetate, or a combination thereof; the water-soluble ligand is a carbohydrate, a hydrogenated carbohydrate, a hydrolysed carbohydrate, a polyol, a polyether, or a combination thereof; and the turbidity point modifier is a complex-forming polyvalence anion.

13. The nanocluster of claim 12, wherein the nanocluster has a particle size of 2 to 80 nm, a turbidity point of 4.5 or lower, and a dissociation rate of 1 to 60 minutes; the water-soluble salt-forming anion is chloride, nitrate, sulfate, acetate, or a combination thereof; the water-soluble ligand is xylitol, robose, mannose, xylose, galactose, fructose, lactose, glucose, mannitol, maltitol, isomaltose, isomalt, sucrose, trehalose, arabinose, sorbitol, polyisomaltose, isomalto oligosaccharide, dextrin, dextran, fructooligosaccharide, or a combination thereof; and the turbidity point modifier is citrate, malate, fumarate, tartrate, lactate, oxalate, succinate, ascorbate, phosphate, pyrophosphate, glycerophosphate, or a combination thereof.

14. A composition comprising a nanocluster of claim 1, wherein the composition has a pH value of 3 to 11.5 and is free of unchelated ions, unreactive water-soluble ligands, and labile low-molecular-weight ion complexes.

15. The composition of claim 14, wherein the nanocluster has a particle size of 2 to 150 nm, a turbidity point of 7 or lower, and a dissociation rate of 1 to 180 minutes; the water-soluble salt-forming anion is fluoride, chloride, bromide, iodide, nitrate, sulfate, acetate, or a combination thereof; the water-soluble ligand is a carbohydrate, a hydrogenated carbohydrate, a polyol, a polyether, or a combination thereof; and the turbidity point modifier is a complex-forming polyvalence anion.

16. The composition of claim 15, wherein the nanocluster has a particle size of 2 to 80 nm, a turbidity point of 4.5 or lower, and a dissociation rate of 1 to 60 minutes; the water-soluble salt-forming anion is chloride, nitrate, sulfate, acetate, or a combination thereof; the water-soluble ligand is xylitol, robose, mannose, xylose, galactose, fructose, lactose, glucose, mannitol, maltitol, isomaltose, isomalt, sucrose, trehalose, arabinose, sorbitol, polyisomaltose, isomalto-oligosaccharide, dextrin, dextran, fructooligosaccharide, or a combination thereof; and the turbidity point modifier is citrate, malate, lactate, fumarate, tartrate, oxalate, succinate, ascorbate, phosphate, pyrophosphate, glycerophosphate, or a combination thereof.

17. The composition of claim 14, wherein the pH value is 3.5 to 9.

18. The composition of claim 17, wherein the nanocluster has a particle size of 2 to 150 nm, a turbidity point of 7 or lower, and a dissociation rate of 1 to 180 minutes; the water-soluble salt-forming anion is fluoride, chloride, bromide, iodide, carbonate, bicarbonate, hydroxide, nitrate, phosphate, pyrophosphate, sulfate, acetate, or a combination thereof; the water-soluble ligand is a carbohydrate, a hydrogenated carbohydrate, a polyol, a polyether, or a combination thereof; and the turbidity point modifier is a complex-forming polyvalence anion.

19. The composition of claim 18, wherein the nanocluster has a particle size of 2 to 80 nm, a turbidity point of 4.5 or below, and a dissociation rate of 1 to 60 minutes; the water-soluble salt-forming anion is chloride, nitrate, sulfate, acetate, or a combination thereof; the water-soluble ligand is xylitol, robose, mannose, xylose, galactose, fructose, lactose, glucose, mannitol, maltitol, isomaltose, isomalt, sucrose, trehalose, arabinose, sorbitol, polyisomaltose, isomalto-oligosaccharide, dextrin, dextran, fructooligosaccharide, or a combination thereof and the turbidity point modifier is citrate, malate, fumarate, tartrate, oxalate, succinate, ascorbate, phosphate, pyrophosphate, glycerophosphate, or a combination thereof.

20. The composition of claim 14, wherein the composition is a transparent aqueous solution or a water-soluble solid capable of being reconstituted into a transparent aqueous solution, the transparent aqueous solution having a pH value of 3.5-9.5.

21. The composition of claim 20, wherein the nanocluster has a particle size of 2 to 150 nm, a turbidity point 7 or lower, and a dissociation rate of 1 to 180 minutes; the water-soluble salt-forming anion is fluoride, chloride, bromide, iodide, nitrate, sulfate, acetate, or a combination thereof the water-soluble ligand is a carbohydrate, a hydrogenated carbohydrate, a polyol, a polyether, or a combination thereof; and the turbidity point modifier is a complex-forming polyvalence anion.

22. The composition of claim 21, wherein the nanocluster has a particle size of 2 to 80 nm, a turbidity point of 4.5 or lower, and a dissociation rate of 1 to 60 minutes; the water-soluble salt-forming anion is chloride, nitrate, sulfate, acetate, or a combination thereof; the water-soluble ligand is xylitol, robose, mannose, xylose, galactose, fructose, lactose, glucose, mannitol, maltitol, isomaltose, isomalt, sucrose, trehalose, arabinose, sorbitol, polyisomaltose, isomalto oligosaccharide, dextrin, dextran, fructooligosaccharide, or a combination thereof; and the turbidity point modifier is citrate, malate, fumarate, tartrate, lactate, oxalate, succinate, ascorbate, phosphate, pyrophosphate, glycerophosphate, or a combination thereof.

23. A method for treating a disorder or for detecting a tissue image, the method comprising administering to a subject in need thereof an effective amount of the nanocluster of claim 1, wherein the disorder is a mineral deficiency disorder, a gastric reflux disorder, or a chronic renal failure and a tissue image is for use in differentiating an abnormal tissue from a normal tissue.

24. A method of preparing a nanocluster of claim 1, the method comprising:
    providing an aqueous dispersion containing X, Y, Z, and OH;
    adjusting the pH of the aqueous dispersion to a predetermined value to obtain a pH-adjusted aqueous dispersion;
    heating the pH-adjusted aqueous dispersion to 50-180° C. so that nanoclusters are formed; and
    adding M after any of the above steps,
    wherein X is a metal cation, Y is a water-soluble salt-forming anion, Z is a water-soluble ligand, M is a turbidity point modifier, and the ratio of X:Y:Z:M is 1:0-9:0.1-10:0.1-9.

25. The method of claim 24, further comprising, after M is added and the nanoclusters are formed, collecting the nanoclusters by nanofiltration and drying the nanoclusters to form solid nanoclusters.

* * * * *